United States Patent [19]

Siret

[11] Patent Number: 5,538,962
[45] Date of Patent: Jul. 23, 1996

[54] ANTIBIOTIC PENEM COMPOUNDS

[75] Inventor: Patrice J. Siret, Reims, France

[73] Assignee: Zeneca Limited, London, England

[21] Appl. No.: 132,256

[22] Filed: Oct. 6, 1993

[30] Foreign Application Priority Data

Oct. 7, 1992 [EP] European Pat. Off. .............. 92402733

[51] Int. Cl.$^6$ ..................... C07D 499/00; A61K 31/425
[52] U.S. Cl. ................ 514/194; 514/195; 540/310
[58] Field of Search ..................... 540/310; 514/210, 514/194, 195

[56] References Cited

U.S. PATENT DOCUMENTS 4,943,569 7/1990 Sunagawa et al. ............ 514/210
5,420,119 5/1995 Kauamoto et al. ............ 540/350

*Primary Examiner*—Nicholas Rizzo
*Attorney, Agent, or Firm*—Cushman Darby & Cushman

[57] ABSTRACT

The present invention provides a compound of the formula (I)

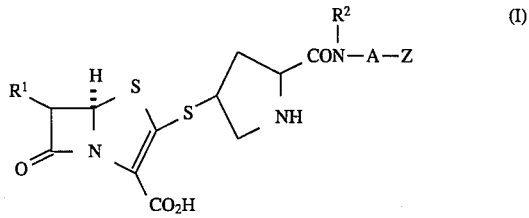

wherein:

$R^1$ is 1-hydroxyethyl, 1-fluoroethyl or hydroxymethyl;

$R^2$ is hydrogen or $C_{1-4}$alkyl;

Z is carboxy, sufonic acid, tetrazol-5-yl or $C_{1-4}$alkylsulfonylcarbamoyl (—$CONHSO_2C_{1-4}$alkyl);

A is a phenyl or thienyl ring;

and A is optionally further substituted by one or two substituents or a pharmaceutically acceptable salt or in vivo hydrolysable ester thereof. Processes for their preparation, intermediates in their preparation, their use as therapeutic agents and pharmaceutical compositions containing them.

8 Claims, No Drawings

ANTIBIOTIC PENEM COMPOUNDS

The present invention relates to penems and in particular to such compounds containing a carboxy substituted phenyl or thienyl group. This invention further relates to processes for their preparation, to intermediates in their preparation, to their use as therapeutic agents and to pharmaceutical compositions containing them. The compounds of this invention are antibiotics and can be used in the treatment of any disease that is conventionally treated with antibiotics for example in the treatment of bacterial infection in mammals including humans.

The present invention provides compounds with a broad spectrum of antibacterial activity including both Gram positive and negative, aerobic and anaerobic bacteria. They exhibit good stability to beta-lactamases. In addition representative compounds of this invention exhibit favourable pharmacokinetics.

The penem derivatives referred to herein are named in accordance with the generally accepted semi-systematic nomenclature:

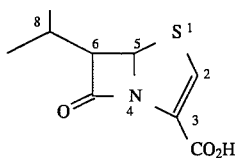

Accordingly the present invention provides a compound of the formula (I)

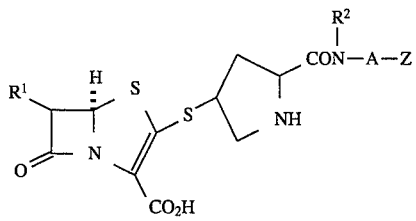

wherein:

$R^1$ is 1-hydroxyethyl, 1-fluoroethyl or hydroxymethyl;

$R^2$ is hydrogen or $C_{1-4}$alkyl;

Z is carboxy, sufonic acid, tetrazol-5-yl or $C_{1-4}$alkylsulfonylcarbamoyl ($-CONHSO_2C_{1-4}$alkyl);

A is a phenyl or thienyl ring;

and A is optionally further substituted by one or two substituents selected from halo, cyano, $C_{1-4}$alkyl, nitro, hydroxy, carboxy, $C_{1-4}$alkoxy, trifluoromethyl, $C_{1-4}$alkoxycarbonyl, amino, $C_{1-4}$alkylamino, di-$C_{1-4}$alkylamino, sulfonic acid, $C_{1-4}$alkylS(0)$_n$—(wherein n is 0–2), $C_{1-4}$alkanoylamino, $C_{1-4}$alkanoyl(N-$C_{1-4}$alkyl)amino, carbamoyl, $C_{1-4}$alkylcarbamoyl, di-$C_{1-4}$alkylcarbamoyl, N-$C_{1-4}$alkanesulfonamido and tetramethylene;

or a pharmaceutically acceptable salt or in vivo hydrolysable ester thereof.

The term alkyl includes all straight and branched chain structures, for example, $C_{1-4}$alkyl includes n-butyl and 2-methylpropyl.

Preferably $R^1$ is 1-hydroxyethyl.

$R^2$ is hydrogen or $C_{1-4}$alkyl for example methyl, ethyl, n-propyl, 1-methylethyl and n-butyl.

Preferably $R^2$ is hydrogen or methyl.

Preferably Z is carboxy.

Preferably, when A is optionally substituted, the optional substituents are selected from halo, cyano, $C_{1-4}$alkyl, nitro, carboxy, hydroxy, $C_{1-4}$alkoxy, carbamoyl, amino and trifluoromethyl.

Suitable substituents for A include, for example:

| | |
|---|---|
| for halo: | fluoro, chloro, bromo and iodo; |
| for $C_{1-4}$alkyl: | methyl, ethyl, propyl, 1-methylethyl, butyl and 2-methylpropyl; |
| for $C_{1-4}$alkoxy: | methoxy, ethoxy, propoxy, 1-methylethoxy, butoxy and 2-methylpropoxy; |
| for $C_{1-4}$alkylcarbamoyl: | methylcarbamoyl, ethylcarbamoyl and propylcarbamoyl; |
| for di-$C_{1-4}$alkylcarbamoyl: | dimethylcarbamoyl and diethylcarbamoyl; |
| for $C_{1-4}$alkylamino: | methylamino, ethylamino and propylamino; |
| for di-$C_{1-4}$alkylamino: | dimethylamino, diethylamino and methylethylamino; |
| for $C_{1-4}$alkylS(O)$_n$-: | methylthio, methylsulfinyl and methylsulfonyl; |
| for $C_{1-4}$alkanoylamino: | acetamido and propionamido; |
| for $C_{1-4}$alkanoyl(N-$C_{1-4}$alkyl)amino: | N-methylacetamido and N-ethylacetamido; |
| for N—$C_{1-4}$alkanesulfonamido: | N-methanesulfonamido and N-ethanesulfonamido. |

The present invention covers all epimeric, diastereoisomeric and tautomeric forms of the compounds of the formula (I) wherein the absolute stereochemistry at the 5-position is as illustrated in formula (I). When a bond is represented as a wedge, this indicates that in three dimensions the bond would be coming forward out of the paper and when a bond is represented as hatched, this indicates that in three dimensions the bond would be going back into the paper. The compounds of the formula (I) have a number of other centres of optical activity, namely: within the group $R^1$ (when $R^1$ is 1-hydroxyethyl or 1-fluoroethyl); at the 6-position; and at the 2'and 4'positions in the pyrrolidine ring:

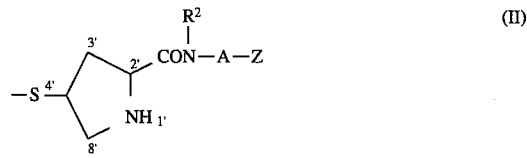

Preferred compounds are those in which the beta-lactam protons are in trans configuration with respect to one another. When $R^1$ is 1-hydroxyethyl or 1-fluoroethyl it is preferred that the 8-substituent has the R-configuration. Thus a preferred class of compounds is that of the formula (III):

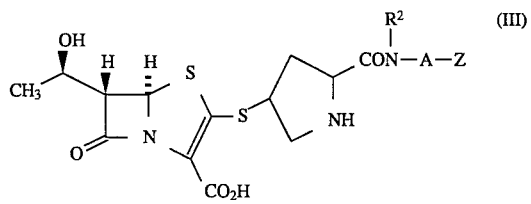

and pharmaceutically acceptable salts and in vivo hydrolysable esters thereof, wherein $R^2$, Z, A and optional substituents on A are as hereinbefore defined.

Preferred compounds are those in which the pyrrolidine ring has the following absolute stereochemistry at the 2'- and 4'-positions:

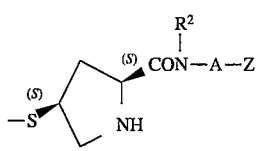

A suitable class of compounds of the present invention is that of the formula (IV):

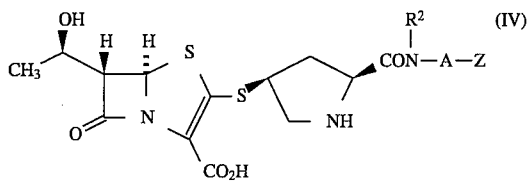

and pharmaceutically acceptable salts and in vivo hydrolysable esters thereof;
wherein $R^2$, Z, A and optional substituents on A are as defined hereinbefore in formula (I).

In another aspect a suitable class of compounds are the compounds of the formula (IV) wherein $R^2$ is hydrogen, methyl or ethyl; and Z, A and optional substituents on A are as defined hereinabove in formula (I).

In yet another aspect a suitable class of compounds is that of the compounds of the formula (IV) wherein A is optionally further substituted by one or two substituents selected from methyl, ethyl, hydroxy, carboxy, cyano, fluoro, chloro, bromo, carbamoyl, nitro, tetramethylene, methoxy, ethoxy and propoxy; Z, A and $R^2$ is as defined hereinbefore in formula (I).

A particular class of compounds of the present invention is that of the formula (IV) wherein:

$R^2$ is hydrogen or methyl;

A is thienyl or phenyl; Z is as hereinbefore defined;
and A is optionally further substituted by one substituent selected from methyl, ethyl, hydroxy, carboxy, cyano, chloro, bromo, nitro, methoxy and ethoxy.

A preferred class of compounds of the present invention is that of the formula (IV) wherein:

$R^2$ is hydrogen;

A is thienyl or phenyl;

Z is carboxy;

and A is optionally further substituted by one substituent selected from methyl, hydroxy, chloro and carboxy.

Another preferred class of compounds of the present invention is that of the formula (IV) wherein:

$R^2$ is hydrogen;

A is thienyl;

Z is carboxy;

and A is not further substituted or substituted.

Another preferred class of compounds of the present invention is that of the formula (IV) wherein:

$R^2$ is hydrogen;

A is phenyl;

Z is carboxy;

and A is not further substituted or substituted.

Particular compounds of the present invention are, for example, the following compounds of the formula (IV): (5R,6S,8R,2'S,4'S)-2-(2-(2-carboxy-4-thienylcarbamoyl)pyrrolidin-4-ylthio)-6-(1-hydroxyethyl)pen-2-em-3-carboxylic acid; (5R,6S,8R,2'S,4'S)-2-(2-(3-carboxyphenylcarbamoyl)pyrrolidin-4-ylthio)-6-(1-hydroxyethyl)pen-2-em-3-carboxylic acid; (5R,6S,8R,2'S,4'S)-2-(2-(2-carboxy-5-thienylcarbamoyl)pyrrolidin-4ylthio)-6-(1-hydroxyethyl)pen-2-em-3-carboxylic acid; and pharmaceutically acceptable salts and in vivo hydrolysable esters thereof.

Suitable pharmaceutically acceptable salts include acid addition salts such as hydrochloride, hydrobromide, citrate, maleate and salts formed with phosphoric and sulfuric acid. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or aminoacids, for example, lysine.

For the avoidance of doubt there may be one, two or three salt-forming cations dependent on the number of carboxylic acid functions and valency of said cations.

Preferred pharmaceutically acceptable salts are sodium and potassium salts. However, to facilitate isolation of the salt during preparation, salts which are less soluble in the chosen solvent may be preferred, whether pharmaceutically acceptable or not.

In vivo hydrolysable esters are those pharmaceutically acceptable esters that hydrolyse in the human body to produce the parent hydroxy or carboxy compound. Such esters can be identified by administering, eg. intravenously to a test animal, the compound under test and subsequently examining the test animal's body fluids. Suitable in vivo hydrolysable esters for hydroxy include acetoxy, propionyloxy, pivaloyloxy, $C_{1-4}$alkoxycarbonyloxy for example ethoxycarbonyloxy, phenylacetoxy and phthalidyl. Suitable in vivo hydrolysable esters for carboxy include $C_{1-6}$alkoxymethyl esters for example methoxymethyl; $C_{1-6}$alkanoyloxymethyl esters for example pivaloyloxymethyl; $C_{3-8}$ cycloalkoxycarbonyloxy$C_{1-6}$alkyl, for example 1-cyclohexyloxycarbonyloxyethyl; 1,3-dioxolen-2-onylmethyl esters for example 5-methyl-1,3-dioxolen-2-onylmethyl; phthalidyl esters and $C_{1-6}$alkoxycarbonyloxyethyl esters for example 1-ethoxycarbonyloxyethyl and may be formed at any carboxy group in the compounds of this invention.

In order to use a compound of the formula (I) or a pharmaceutically acceptable salt or in vivo hydrolysable ester thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt or in vivo hydrolysable ester thereof and a pharmaceutically acceptable carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, emulsions, dispersible powders, suppositories and sterile injectable aqueous or oily solutions or suspensions.

The compounds of the present invention may be formulated as dry powder filled vials, which may contain the compound of the present invention alone or as a dry blended mixture. For example an acidic compound of the present invention may be dry blended with an alkali metal carbonate or bicarbonate. Freeze dried formulations of compounds of the present invention, alone or as a mixture with standard excipients, are possible. Standard excipients include structure formers, cryoprotectants and pH modifiers, such as, mannitol, sorbitol, lactose, glucose, sodium chloride, dextran, sucrose, maltose, gelatin, bovine serum albumin (BSA), glycine, mannose, ribose, polyvinylpyrrolidine (PVP), cellulose derivatives, glutamine, inositol, potassium glutamate, erythritol, serine and other amino acids and buffer agents e.g. disodium hydrogen phosphate and potassium citrate.

In addition to the compounds of the present invention the pharmaceutical composition of this invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenecid) and inhibitors of metabolising enzymes (for example inhibitors of dehydropeptidases, for example Z-2-acylamino-3-substituted propenoates such as cilastatin) and -acylated amino acids such as betamipron (also see EP-A-178911).

A suitable pharmaceutical composition of this invention is one suitable for oral administration in unit dosage form, for example a tablet or capsule which contains between 100 mg and 1 g of the compound of this invention.

A preferred pharmaceutical composition of the invention is one suitable for intravenous, subcutaneous or intramuscular injection, for example a sterile injectable composition containing between 1 and 50% w/w of the compound of this invention.

Specific examples of compositions, which are constituted as a 1% solution in water, freeze dried and may be made up by adding 0.9% aqueous sodium chloride solution to give the required concentration, preferably 1 mg–10 mg/ml, are as follows:

| Composition 1 | |
|---|---|
| Compound of Example 1 | 50 mg |
| Composition 2 | |
| Compound of Example 1 | 50 mg |
| Glycine | 31 mg |

Further specific examples of compositions are as above, but where the compound of example 1 is replaced by example 2 or 3.

The pharmaceutical compositions of the invention will normally be administered to man in order to combat infections caused by bacteria, in the same general manner as that employed for imipenem due allowance being made in terms of dose levels for the pharmacokinetics of the compound of the present invention relative to the clinical use of imipenem. Thus each patient will receive a daily intravenous, subcutaneous or intramuscular dose of 0.05 to 5 g, and preferably 0.1 to 2.5 g, of the compound of this invention, the composition being administered 1 to 4 times per day, preferably 1 or 2 times a day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a suitable daily oral dose is 0.05 to 5 g. of the compound of this invention, the composition being administered 1 to 4 times per day.

In a further aspect the present invention provides a process for preparing the compounds of the formula (I) or a pharmaceutically acceptable salt or in vivo hydrolysable ester thereof which process comprises deprotecting a compound of the formula (V) wherein A is optionally further substituted as in formula (I):

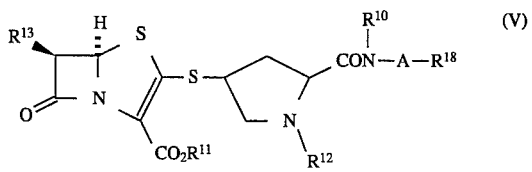

and wherein A is as hereinbefore defined; $R^{10}$ is a group or an amino protecting group; $R^{13}$ is a group $R^1$ protected hydroxymethyl or 1-(protected hydroxy)ethyl; $R^{11}$ is hydrogen or a carboxy protecting group; $R^{12}$ is hydrogen or an amino protecting group, $R^{18}$ is Z or a protected Z group and wherein any optional substituent on A is optionally protected; and wherein at least one protecting group is present; and thereinafter if necessary;

(i) forming a pharmaceutically acceptable salt, (ii) esterifying to form an in vivo hydrolysable ester.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

The compounds of the formula (V) are novel and form another aspect of the invention.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1–12C)alkyl groups (eg isopropyl, t-butyl); lower alkoxy lower alkyl groups (eg methoxymethyl, ethoxymethyl, isobutoxymethyl); lower aliphatic acyloxy lower alkyl groups, (eg acetoxymethyl, propionyloxymethyl, butyryloxymethyl, pivaloyloxymethyl); lower alkoxycarbonyloxy lower alkyl groups (eg 1-methoxycarbonyloxyethyl, 1-ethoxycarbonyloxyethyl); aryl lower alkyl groups (eg p-methoxybenzyl, o-nitrobenzyl, p-nitrobenzyl, benzhydryl and phthalidyl); tri(lower alkyl)silyl groups (eg trimethylsilyl and t-butyldimethylsilyl); tri(lower alkyl)silyl lower alkyl groups (eg trimethylsilylethyl); diaryl(lower alkyl)silyl groups (eg t-butyldiphenylsilyl); and (2–6C)alkenyl groups (eg allyl and vinylethyl).

Methods particularly appropriate for the removal of carboxyl protecting groups include for example acid-, base-, metal- or enzymically-catalysed hydrolysis, for groups such as p-nitrobenzyloxycarbonyl, hydrogenation and for groups such as o-nitrobenzyloxycarbonyl, photolytically.

Examples of hydroxy protecting groups include lower alkenyl groups (eg allyl); lower alkanoyl groups (eg acetyl); lower alkoxycarbonyl groups (eg t-butoxycarbonyl); lower alkenyloxycarbonyl groups (eg allyloxycarbonyl); aryl lower alkoxycarbonyl groups (eg benzoyloxycarbonyl, -methoxybenzyloxycarbonyl, o-nitrobenzyloxycarbonyl, p-nitrobenzyloxycarbonyl); tri lower alkylsilyl (eg trimethylsilyl, t-butyldimethylsilyl); diaryl(lower alkyl)silyl (eg t-butyldiphenylsilyl) and aryl lower alkyl (eg benzyl) groups.

Examples of amino protecting groups include formyl, aralkyl groups (eg benzyl and substituted benzyl, eg p-methoxybenzyl, nitrobenzyl and 2,4-dimethoxybenzyl, and triphenylmethyl); di-p-anisylmethyl and furylmethyl groups; lower alkoxycarbonyl (eg t-butoxycarbonyl); lower alkenyloxycarbonyl (eg allyloxycarbonyl); aryl lower alkoxycarbonyl groups (eg benzyloxycarbonyl, p-methoxybenzyloxycarbonyl, o-nitrobenzyloxycarbonyl, p-nitrobenzyloxycarbonyl); trialkylsilyl (eg trimethylsilyl and t-butyldimethylsilyl); diaryl(lower alkyl)silyl (eg t-butyldiphenylsily); alkylidene (eg methylidene); benzylidene and substituted benzylidene groups.

Methods appropriate for removal of hydroxy and amino protecting groups include, for example, acid-, base-, metal- or enzymically-catalysed hydrolysis, for groups such as p-nitrobenzyloxycarbonyl, hydrogenation and for groups such as o-nitrobenzyloxycarbonyl, photolytically.

In another aspect of the present invention the compounds of the formulae (I) and (V) may be prepared by a) reacting compounds of the formulae (VI) and (VII):

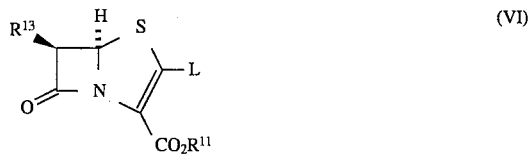

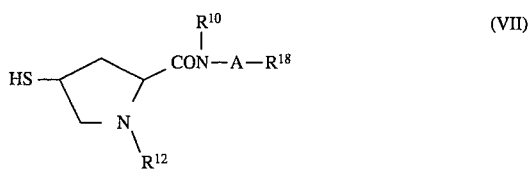

wherein A, $R^{10}$ $R^{11}$ $R^{12}$ $R^{13}$ and $R^{18}$ are as hereinbefore defined optional substituents on A are as hereinbefore defined and L is a leaving group, or b) cyclising a compound of the formula (VIII):

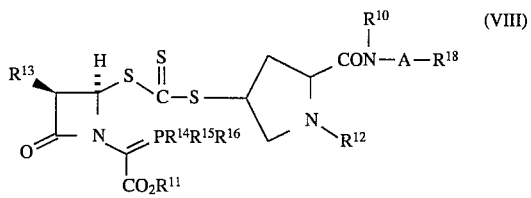

wherein A, $R^{10}$, $R^{11}$, $R^{12}$, $R^{13}$ and $R^{18}$ are as hereinbefore defined optional substituents on A are as hereinbefore defined and $R^{14}$, $R^{15}$ and $R^{16}$ are independently selected from aryl and $C_{1-6}$alkoxy; and wherein any functional group is optionally protected and thereinafter if necessary:

(i) removing any protecting groups;
(ii) forming a pharmaceutically acceptable salt;
(iii) esterifying to form an in vivo hydrolysable ester.

Suitably in the compound of the formula (VI), L is the reactive ester of a hydroxy group such as a sulfonate (for example trifluoromethanesulfonyloxy). In an alternative L is a sulfoxide for example —SOCH=CH—NHCOCH$_3$ or —SOC$_2$H$_5$ which may be readily displaced. Preferably L is —SOC$_2$H$_5$.

Compounds of the formula (VI) and their preparation are well known in the penem literature, for example see EP-199490, J. Antibiotics 1987, 1636 and Tet. Lett. 1982, 23, 3535.

When L is trifluoromethanesulfonyl, the compounds of the formula (VI) may be prepared by reacting a compound of the formula (XIX) with trifluoromethanesulfonic anhydride:

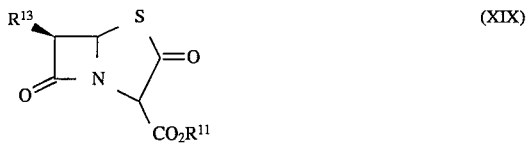

wherein $R^{11}$ and $R^{13}$ are as hereinbefore defined. For an analagous reaction see *Tet. Lett.* 1990, 31, 3291.

The compounds of the formula (XIX) may be prepared by cyclising compounds of the formula (XX):

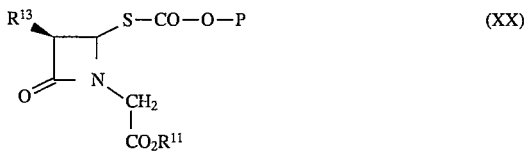

wherein $R^{11}$ and $R^{13}$ are as hereinbefore defined and P is a carboxy protecting group. The cyclisation typically takes place in the presence of a base such as lithium hexamethyldisilyl. For an analagous example see *Tet. Lett.* 1990, 31, 3291.

Compounds of the formula (VI) wherein L is an alkylsulfoxide may be prepared by alkylating and subsequently oxidising compounds of the formula (XXI):

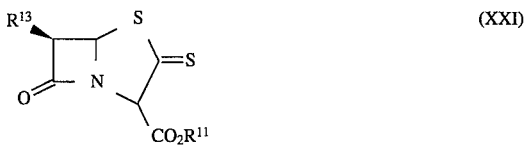

wherein $R^{11}$ and $R^{13}$ are as hereinbefore defined. Alkylation is carried out under standard conditions known in the art, for example, by reacting with an alkylhalide, such as ethyliodide, in the presence of a base. Reagents and conditions for oxidising the resulting sulfide to a sulfoxide are known in the art. For example in dichloromethane with m-chloroperoxybenzoic acid as the oxidating agent.

The reaction between the compounds of the formulae (VI) and (VII) is typically performed in the presence of a base such as an organic amine for example di-isopropylethylamine or an inorganic base for example an alkali metal carbonate such as potassium carbonate. The reaction is conveniently performed at a temperature between −25° C. and ambient. The reaction is generally performed in an organic solvent such as acetonitrile or dimethylformamide. The reaction is generally performed in a manner similar to that described in the literature for similar reactions.

The compounds of the formula (VII) may be prepared by the deprotection of a compound of the formula (IX):

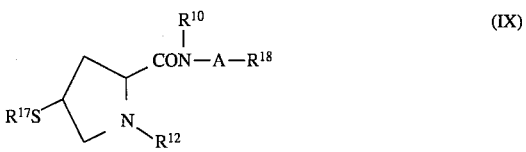

wherein A, $R^{10}$, $R^{12}$ and $R^{18}$ are as hereinbefore defined, optional substitutents on A are as hereinbefore defined and $R^{17}$ is a protecting group, for example $C_{1-6}$alkanoyl or $C_{1-6}$alkoxycarbonyl. Preferred values for $R^{17}$ are acetyl and t-butoxycarbonyl. The compounds of the formula (IX) can be converted to the compounds of the formula (VII) by standard methods of deprotection, for example acetyl groups can be removed by basic hydrolysis in aqueous alkanol, alkenol for example allyl alcohol or tetrahydrofuran.

The compounds of the formula (IX) may be prepared by the reaction of an activated derivative of a compound of the formula (X), which may be formed in situ, with a compound of the formula (XI):

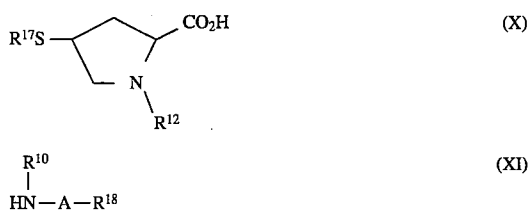

(X)

(XI)

wherein A, $R^{10}$, $R^{12}$, $R^{17}$ and $R^{18}$ are as hereinbefore defined and optional substitutents on A are as hereinbefore defined. Activated derivatives of the compound of the formula (X) include acid halides, anhydrides and 'activated'esters such as 1H-benzol-1,2,3triazol-1-yl, pentafluorophenyl and 2,4,5-trichlorophenyl esters or the benzimidazol-2-yl ester of the thiocarboxylic acid corresponding to (X). The reaction of the compounds of the formulae (X) and (XI) is performed under standard methods, for example in the presence of sulfonyl chloride at ambient temperature.

The compounds of the formulae (X) and (XI) are prepared by standard methods known to the skilled chemist such as the methods of the Examples hereinafter, the methods described in EP-A-126587 or by methods analogous or similar thereto.

Suitably, in the compounds of the formula (VIII), $R^{14}$ $R^{15}$ and $R^{16}$ are independently selected from aryl such as phenyl or $C_{1-6}$ alkoxy such as methoxy, ethoxy, isopropoxy, n-propoxy or n-butoxy; Preferably each of $R^{14}$-$R^{16}$ have the same value and are $C_{1-6}$alkoxy for example methoxy, ethoxy, isopropoxy or n-butoxy or aryl for example phenyl.

The compounds of the formula (VIII) are cyclized under conventional conditions known in the art to form compounds of the formula (V). Typical conditions are heating in a substantially inert organic solvent such as toluene, xylene or ethyl acetate at temperatures in the region 60°–150° C. Typically the reaction is performed in an atmosphere of nitrogen and is carried out in the presence of a radical scavenger for example hydroquinone. For examples see Chem. Pharm. Bull. 1983, 31, 768 and Chem. Pharm. Bull. 1990, 38, 1077.

The compounds of the formula (VIII) may be formed and cyclized in situ. The compounds of the formula (VIII) may conveniently be prepared by reacting compounds of the formulae (XII) and (XIII):

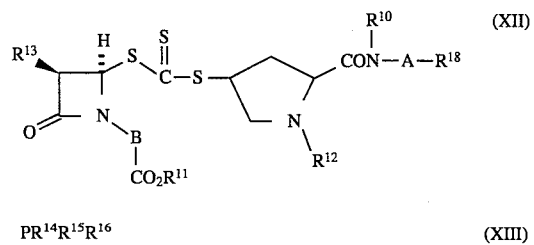

(XII)

$PR^{14}R^{15}R^{16}$ (XIII)

wherein A, $R^{10}$, $R^{11}$ $R^{16}$, $R^{18}$ and optional substituents are as hereinbefore defined and B is CO or when $R^{14}$-$R^{16}$ are phenyl, CHCl. Suitably the compound of the formula (XIII) is a phosphite or is the functional equivalent of such a compound.

The reaction between the compounds of the formulae (XII) and (XIII) is conveniently performed in an organic solvent such as toluene, xylene, ethyl acetate, chloroform, dichloromethane or acetonitrile. Typically the reaction is carried out at an elevated temperature for example 60°–150° C., preferably 110°–120°.

The compounds of the formula (XII) may be prepared by a number of methods known in the art. For example the compounds of the formula (XII) may be prepared by the acylation of a compound of the formula (XIV):

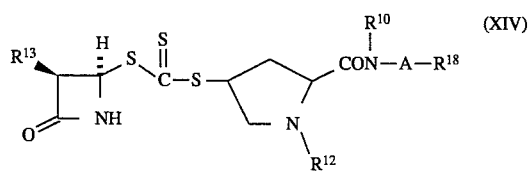

(XIV)

wherein A, $R^{10}$, $R^{12}$, $R^{13}$, and $R^{18}$ are as hereinbefore defined and optional substitutents on A are as hereinbefore defined with a compound of the formula (XVA) when B is CO and a compound of the formula (XVB) (subsequently converting the hydroxy group to a chloro group), when B is CHCl:

Cl-CO-COOR$^{11}$ (XVA)

CHOCOOR$^{11}$ (XVB)

wherein $R^{11}$ is as hereinbefore defined and conversion of the hydroxy group to a chloro group is conveniently effected by reacting with a chloronating agent such as sulfonyl chloride in the presence of a base.

The compounds of the formula (XIV) may be prepared by reacting compounds of the formulae (XVI) and (XVII):

(XVI)

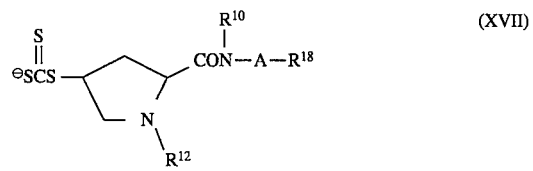

(XVII)

wherein $R^{10}$, $R^{12}$, $R^{13}$ and $R^{18}$ are as hereinbefore defined. The compounds of the formula (XVI) are known in the art and may be reacted with the compounds of the formula (XVII) under conventional methods known in the art.

Compounds of the formula (XVII) may be prepared by reacting compounds of the formula (VII) with $CS_2$ in the presence of a base such as potassium hydroxide. The reaction is performed under standard conditions known in the art, for example, see Helv. C. A. 1980, 63, 1093.

Compounds of the formulae (XII) and (XIV) are novel and, as such, form another aspect of this invention.

The following biological test methods, data and Examples serve to illustrate the present invention.

Antibacterial Activity

The pharmaceutically acceptable penem compounds of the present invention are useful antibacterial agents having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system. In particular the penems of the present invention show good stability to beta-lactamases and in general particularly good pharmacokinetics, especially as regards half life.

The antibacterial properties of the compounds of the invention may also be demonstrated in vivo in conventional tests. In the following examples:

Penem compounds have generally been found to be relatively non-toxic to warm-blooded animals, and this generalisation holds true for the compounds of the present invention. Compounds representative of the present invention were administered to mice at doses in excess to those required to afford protection against bacterial infections, and no overt toxic symptoms or side effects attributable to the administered compounds were noted.

The following results were obtained for representative compounds on a standard in vitro test system using Diagnostic Sensitivity Test. The antibacterial activity is described in terms of the minimum inhibitory concentration (MIC) determined by the agar-dilution technique with an inocukum size of $10^4$ CFU/spot.

| | MIC (mg/L) | |
| --- | --- | --- |
| ORGANISM | EXAMPLE 1 | ceftriaxone |
| Enterobacter cloacae 029 | 0.015 | 0.06 |
| Enterbacter cloacae 108 | 0.5 | 32 |
| E. coli TEM | 0.008 | 0.03 |
| S. aureus 147N | 0.125 | 2.0 |

(a) allyloxy means the propen-1-yloxy group —$OCH_2CH=CH_2$;
(b) THF means tetrahydrofuran;
(c) DMF means dimethylformamide; and
(d) evaporation of solvents was carried out under reduced pressure.

EXAMPLE 1

(5R,6S,8R,2'S,4'S)-2-(2-(2-carboxy-4-thienylcarbamoyl) pyrrolidin-4-ylthio)-6-(1-hydroxyethyl)pen-2-em-3-carboxlic acid To a solution of allyl (5R,6S,8R,2'S,4'S)-2-(1-(4-nitrobenzyloxycarbonyl)- 2-(2-allyloxycarbonyl-4-thienylcarbomoyl)pyrrolidin-4-ylthio)-6-(1-hydroxyethyl)pen-2-em-3-carboxylate (559 mg; 0.651 mol; 1 eq.) in DMF (19 ml) were added $PPh_3$ (34 mg; 0.13 mol; 0.2 eq.), tetrakistriphenylphosphine palladium (34 mg) and a solution of sodium 2-ethylhexanoate in ethyl acetate (3.5 ml; 0.43M; 1.49 mmol; 2.3 eq.). After 20 minutes the mixture was concentrated to dryness, under vacuum. The residue was taken up in a mixture of ethyl acetate/water (30 ml 30 ml) and hydrogenated in the presence of 10% palladium on carbon (600 mg) for 3 hours. The catalyst was filtered off on celite and washed with water. The aqueous phase was decanted, extracted with ethyl acetate 5 ml and then freeze-dried. The residue was purified on a silica gel C18 column, eluting with water, then with 5% $CH_3CN$ in water. The phases were concentrated then freeze-dried to give the title compound (sodium salt) as a foam (229 mg). NMR (DMSO-d6+AcOH–80C): δ1.17 (d, 3H); 1.78–1.86 (m, 1H); 2.57–2.60 (m, 1H); 2.84–2.88 (m, 1H); 3.39–3.43 (m, 1H); 3.62–3.67 (m, 3H); 3.80–3.84 (m, 1H); 3.95–3.98 (m, 1H); 5.61 (d, 1H J =1.47 Hz); 7.61 (d, 1H); 7.69 (d, 1H).

MS (FAB DMSO) M+$Na^+$—$H^+$=530

The starting material was prepared as follows:

2-Thiophenecarboxylic acid (6.4 g, 50 mM) was suspended in acetic anhydride (15 ml) and fuming nitric acid (16 ml) in glacial acetic acid (25 ml) added slowly over 1 hour with stirring, while keeping the temperature of the reaction mixture below 30° C. The reaction mixture was stirred at ambient temperature for 2 hours. The product was purified by subjecting to chromatography (470 ml) on HP20SS resin using methanol/(water +1% acetic acid): 0/100→50/50 as eluant. Pure 4-nitro-2-thiophenecarboxylic acid was obtained (1.3 g) together with a mixture of 4- and 5-nitrothiophene-2-carboxylic acid (4.4 g). NMR ($CDCl_3$): δ8.35 (d, 1H); 8.5 (d, 1H).

4-Nitro-2-thiophenecarboxylic acid (1 g, 5.7 mmol) was added with stirring to a solution of $SnCl_2 \cdot 2H_2O$ (3.25 g, 14.4 mmol) in concentrated HCl (10 ml). The mixture was stirred for 6 hours at ambient temperature and purified by subjecting to chromotography on HP20SS resin, using water as eluant, to give 4-amino-2-thiophenecarboxylic acid (0.59 g, 71%). NMR (DMSO-$d_6$+AcOD-$d_4$): δ7.6 (s, 2H).

(2S,4S)-4-Acetylthio-2-carboxy-1-(4-nitrobenzyloxycarbonyl)pyrrolidine (1.5 g, 4.08 mmol) was dissolved at ambient temperature in thionyl chloride (10 ml). The mixture was stirred for 4 hours at ambient temperature. The thionyl chloride was evaporated, the residual oil taken up in dichloromethane/toluene (10 ml, 1:1) and the solvent removed by evaporation. The residual oil was dried under vacuum for 1 hour and dissolved in dichloromethane (25 ml). This solution was added to a mixture of 4-amino-2-thiophnecarboxylic acid (0.58 g, 4.08 mmol), trimethylsilyl chloride (1 ml, 8.2 mmol) and diisopropylethylamine (3 ml, 17.25 mmol) in dichloromethane (40 ml) at 0° C. The reaction mixture was stirred for 12 hours at ambient temperature, the solvent evaporated and the residue dissolved in DMF and subjected to chromatgraphy on HP20SS resin, eluting with acetonitrile/water/acetic acid (40:60:1), followed by concentration and lyophilisation to give (2S,4S)-1-(4-Nitrobenzylcarbonyl)-2-(2-carboxy-4-thienylcarbamoyl)-pyrrolidin-4-ylthioacetate (0.84 g, 42%).

NMR (DMSO-$d_6$+AcOD-$d_4$): δ1.92 (m, 1H), 2.32 (s, 3H), 2.76 (m, 1H), 3.35 (m, 1H); 3.9–4.2 (m, 2H); 4.42 (m, 1H); 5.0–5.35 (m, 2H); 7.45 (d, 1H); 7.65 (d, 1H); 7.76 (s, 2H); 7.96 (d, 1H); 8.22 (d, 1H).

(2S,4S)-1-(4-Nitrobenzyloxycarbonyl)-2-(2-carboxy-4-thienylcarbamoyl)pyrrolidin- 4-ylthioacetate (0.475 g, 0.963 mmol) was dissolved in a mixture of dioxane/water (1:1) (20 ml) and treated with a 1M aqueous solution of NaOH (2.5 ml, 2.4 mmol). The reaction was monitored by HPLC. After 1 hour, the pH was adjusted to pH3 with a 6M aqueous solution of HCl, at 0°. The reaction mixture then was evaporated and dried over vacuum for 1 hour, to give (2S,4S)-1-(4-nitrobenzyloxycarbonyl) 2-(2-carbox-4-thienylcarbamoyl)pyrrolidin-4-yl thiol.

To a solution of (2S,4S)-1-(4-nitrobenzyloxycarbonyl)-2-(2-carboxy-4-thienylcarbamoyl)pyrrolidin-4ylthiol (2.25 g; 4.58 mmol; 1.2 eq.) in acetonitrile (15 ml) under argon atmosphere were added allyl (5R,6S,8R)-2-(ethylsulfonyl)-6-(1-(tert-butyldimethylsilyloxy)-ethyl)pen-2-em-3-carboxylate (1.7 g; 3.82 mmol; 1.0 eq.), N-ethyl-diisopropylamine (88 ul; 4.58 mmol; 1.2 eq.) [F. DiNinno et al, Tet. Lett. 1982, 23, 3535], tri-n-butylphosphine (190 ul; 0.76 mmol; 0.2 eq.), water (14 ul; 0.76 mmol; 0.2 eq.). After stirring for one hour the solvents were evaporated. The residue was purified by flash chromatography, eluting with ethyl acetate in petroleum ether (45 to 55%) to give allyl (5R,6S,8R,2'S,4'S)-2-(1-(4-nitrobenzyloxycarbonyl)-2-(2-allyloxycarbonyl-4-thienylcarbamoyl)pyrrolidin-4-ylthio)-6-(1-(tertbutyldimethylsilyloxy) ethyl)pen-2-em-3-carboxylate as a light yellow solid (1.43 g; 44%).

NMR (DMSO-$d_6$; 100C): δ0.0 (2s, 6H); 0.8 (s, 9H); 1.18 (d, 3H); 1.9–2.0 (m, 1H); 2.75–2.85 (m, 1H); 3.4–3.5 (m, 1H); 3.8–3.95 (m, 2H); 4.1–4.2 (m, 2H); 4.35–4.42 (m, 1H); 4.45–4.6 (m, 1H); 4.65–4.75 (m, 2H); 5.05–5.4 (m, 6H); 5.65 (m, 1H); 5.75–6.0 (m, 2H); 7.45–7.5 (m, 2H); 7.65 (m, 1H); 7.75 (m, 1H); 7.95–8.05 (m, 2H).

To a solution of allyl (5R,6S,8R,2'S,4'S)-2-(1-(4-nitrobenzyloxycarbonyl- 2-(2-allyloxycarbonyl-4-thienylcarbamoyl)pyrroldin-4-ylthio)-6-(1-(tert-butyldimethylsilyloxy)ethyl)pen-2-em-3-carboxylate (1.4 g; 1.63 mmol; 1 eq.) in THF (21 ml) cooled in a ice bath, were added acetic acid (1.86 ml; 32.6 mmol; 20 eq.), and tetrabutylammonium fluoride (16.38 ml; solution 1M in THF; 16.38 mmol; 10 eq.) dropwise. The solution was left overnight at ambient temperature. After concentration, the residue was diluted with ethyl acetate, washed twice with saturated aqueous $NaHCO_3$ solution, water, brine, dried over $MgSO_4$ and concentrated. The residue was purifed on silica. Elution with $CH_3CN$/$CH_2Cl_2$ (35/65) gave allyl (5R,6S,8R,2'S,4'S)-2-(-1-(4-nitrobenzyloxycarbonyl)-2-(2-allyloxycarbonyl- 4-thienylcarbamoyl)pyrrolidin-4-4ylthio)-6-(1-hydroxyethyl pen-2-em-3-carboxylate as a solid (780 mg; 63%).

NMR (DMSO-$d_6$, 80C): δ1.2 (d, 3H); 2.0–2.1 (m, 1H); 2.8–2.9 (m, 1H); 3.5–3.55 (m, 1H); 3.8 (d, 1H); 3.95–4.05 (m, 2H); 4.15–4.25 (m, 2H); 4.4–4.7 (m, 3H); 4.75 (d, 2H); 5.1–5.4 (m, 6H); 5.75 (d, 1H); 5.8–5.9 (m, 1H); 5.95–6.1 (m, 1H); 7.45–7.65 (m, 2H); 7.75 (s, 1H); 7.85 (s, 1H); 7.95–8.2 (m, 2H).

EXAMPLE 2

(8R,6S,8R,2'S,4'S)-2-(2-(3-Carboxyphenylcarbamoyl) pyrrolidin-4-ylthio)-6-(1-hydroxyethyl)pen-2-em-3-carboxylic acid.

To a solution of allyl (5R,6S,8R,2'S,4'S)-2-(1-(4-nitrobenzyloxycarbonyl)- 2-(3-allyloxycarbonylphenylcarbamoyl)pyrrolidin-4-ylthio) -6-(1-hydroxyethyl)pen-2-em-3-carboxylate (303 mg, 0.4 mmol) in DMF (10 ml) were added, successively, triphenylphosphine (20 mg, 0.2 equivalents), sodium 2-ethylhexanoate in ethyl acetate (2 ml, 0.45M, 2.3 equivalents) and tetrakistriphenylphosphine palladium (20 mg). After 30 minutes the solvent was evaporated and the residue taken up in ethyl acetate/water (1:1, 24 ml) and hydrogenated in the presence of 10% palladium on carbon (300 mg) for one hour. The mixture was filtered through celite and the aqueous phase decanted and extracted with ethyl acetate then lyophilised.

The residue was purified on a silica gel $C_{18}$ column, eluting with a gradient of 0–6% $CH_3CN$ in $(NH_4)_2CO_3$ buffer (2 g/L, pH 6.0). The fractions were concentrated then lyophilised to give the title compound as a white solid (35 mg).

NMR (DHSO-$d_6$ +AcOD; 50° C.): δ1.17 (d, 3H); 1.8–1.9 (br, 1H); 2.6–2.7 (br, 1H); 2.90–2.95 (br, 1H); 3.4–3.5 (br, 1H); 3.65–3.70 (br, 1H); 3.75 (d, 1H); 3.85–3.90 (br, 1H); 3.95–4.00 (br, 1H); 5.68 (d, 1H); 7.4 (t, 1H); 7.8 (m, 1H), 8.25 (s, 1H). MS (FAB) M+H$^+$=530.

The starting material was prepared as follows:

3-Nitrobenzoic acid (2.6 g, 21.3 mH) was dissolved in DHF (55 ml), and anhydrous $K_2CO_3$ (11.78 g, 76.5 mM) added with stirring. Allyl bromide (5.4 ml, 62.4 mM) was run in, and the mixture stirred for 18 hours at ambient temperature. The solvent was removed by evaporation, the residue treated with water, the pH adjusted to 5.5, and product extracted into ethyl acetate. The combined extracts were washed with aqueous $NaH_2PO_4$, water, brine, and dried over $MgSO_4$. The residue, after evaporation, was subjected to chromatography on silica, eluting with a mixture of petrol/EtOAc (10:1), to give allyl 3-nitrobenzoate.

NMR ($CDCl_3$): δ4.88 (d, 2H); 5.33–5.49 (m, 2H); 5.96–6.17 (m, 1H); 7.66 (t, 1H); 8.41 (td, 2H); 8.88 (t, 1H).

Stannous chloride dihydrate was refluxed in ethanol, under an argon blanket, to give a solution. The heat was removed, and the above nitro compound in ethanol was run in. Refluxing was then continued for 3 hours, the mixture cooled, and solvents removed. The residue was dissolved in ethyl acetate, and treated with 880 ammonia until basic. The organic phase was decanted from precipitated tin salts, and the slurry re-extracted similarly with more solvent. Combined organic phases were then washed with diluted ammonia, water, and brine, before drying over $MgSO_4$. Evaporation gave allyl 3-aminobenzoate.

NMR ($CDCl_3$): δ3.38 (br, 2H); 4.79 (dt, 2H); 5.24–5.44 (m, 2H); 5.93–6.09 (m, 1H); 6.86 (dm, 1H); 7.21 (t, 1H); 7.37 (t, 1H); 7.45 (dt, 1H).

Preparation of Side Chain Pyrrolidin-4-ylthioacetate (2S,4S)-4-Acetylthio-1-allyloxycarbonyl-2-carboxypyrrolidine (2.54 g, 9.3 mM), allyl 3-aminobenzoate (1.5 g, 8.5 mM), and 2-ethoxy-1-ethoxycarbonyl-1,2-dihydroquinoline (2.72 g, 11 mM) were dissolved in toluene (50 ml) and stirred for 18 hours at ambient temperature. The reaction mixture was diluted with ethyl acetate (150 ml) and washed with 2M HCl (3 by 30 ml), water, saturated $NaHC_{O3}$, and brine. Drying over $MgSO_4$ and evaporation gave (2S,4S)-4-acetylthio-1-allyloxycarbonyl-2-(3-allyloxycarbonylphenylcarbamoyl)pyrrolidine as a gum (3.7 g, 100%) in a state sufficiently pure for further work.

NMR ($CDCl_3$): δ2.32 (s, 3H); 2.60 (br, 2H), 3.40 (dd, 1H); 4.03 (quintet, 1H); 4.13 (dd, 1H); 4.57 (t, 1H); 4.66 (dm, 2H); 4.82 (dt, 2H); 5.23–5.46 (m, 4H); 5.86–6.12 (m, 2H); 7.41 (t, 1H); 7.82 (d, 1H), 8.07 (t, 1H); 9.18 (br, 1H).

An 2M aqueous solution of sodium hydroxide (960 μl, 1.19 mmol, 1.1 equivalents) was added portionwise to a solution of the thioacetate (916 mg, 1.74 mmol) in allyl alcohol (17 ml) and cooled on ice. The mixture was then stirred at ambient temperature for 45 minutes and hydrochloric acid (2N, 960 μl) added. The mixture was concentrated by evaporating the solvent, the residue taken up in ethyl acetate, washed twice with brine, dried with $MgSO_4$ and the solvent was evaporated. The residue was taken up in acetonitrile (6 ml) and allyl (5R,6S,8R)-2-(ethylsulphonyl)-6-(1-tert-butyldimethylsilyloxy)ethyl)pen-2-em-3-carboxylate (645 mg, 1.45 mmol) [prepared as described in F Di Ninno et al Tet. Lett. 1982, 23, 3535], tri-n-butylphosphine (87 μl, 0.2 equivalents), water (6 μl, 0.2 equivalents) and N-ethyldiisopropylamine (305 μl, 1.2 equivalents). After 45 minutes at ambient temperature, the solvents were evaporated, the dry residue taken up in ethyl acetate, washed with water, washed with brine, dried with $MgSO_4$ and the solvent evaporated. The residue was purified on a silica column eluting with ethyl acetate/petroleum ether (1:1) to give allyl (5R,6S;8R,2'S,4'S)-2-(1-(4-nitrobenzyloxycarbonyl)-2-(3 -allyloxycarbonylphenylcarbamoyl)pyrrolidin-4-ylthio)-6-(1-(tert-butyldimethylsilyloxy) ethyl)pen-2-em-3-carboxylate (636 mg, 52%).

NMR (DMSO-d$_6$, 60° C.): δ0.1 (s, 9H); 0.9 (s, 6H); 1.2 (d, 3H); 2.0–2.1 (br, 1H); 2.85–2.95 (br, 1H); 3.65–3.70 (br, 1H); 3.95 (d, 1H); 3.95–4.10 (br, 1H); 4.2–4.3 (br, 2H); 4.4–4.6 (br, 1H); 4.55–4.70 (m, 2H); 4.80 (m, 2H); 5.10–5.45 (m, 6H); 5.75 (d, 1H); 5.80–5.95 (m, 1H); 6.00–6.15 (m, 1H); 7.4–7.5 (br, 2H); 7.6–7.7 (br, 2H); 7.8–8.0 (br, 2H); 8.1–8.3 (br, 2H).

To a solution of allyl (5R,6S,8R,2'S,4'S)-2-(1-(4-nitrobenzyloxycarbonyl)-2-(3-allyloxycarbonylphenylcarbamoyl)pyrrolidin-4-ylthio)-6-(1-(tert-butyldimethylsilyloxy)ethyl)pen-2-em-3-carboxylate (626 mg, 0.734 mmol) in THF (10 ml) were added acetic acid (740 μl 20 equivalents) and a (1M) solution of tetrabutylammonium fluoride in THF (7.3 ml, 10 equivalents). The mixture was left overnight at ambient temperature then concentrated, diluted with ethyl acetate, washed with water, then saturated aqueous sodium bicarbonate solution, then water then brine. The solution was dried with MgSO$_4$ and the solvent evaporated to give allyl (5R,6S,8R,2'S,4'S)-2-(1-(4-nitrobenzyloxycarbonyl)-2-(3-allyloxycarbonylphenylcarbamoyl)pyrrolidin-4-ylthio)-6-(1-hydroxyethyl)pen-2-em-3-carboxylate (303 mg) which was used in the subsequent deprotection step without further purification.

EXAMPLE 3

(5R, 6S8R, 2'S4'S)-2-(2-(2-carboxy-5-thienylcarbamoyl) pyrrolidin-4-ylthio)-6-(1-hydroxy)pen-2-em-3-carboxylic acid.

To a solution of allyl (5R,6S,8R,2'S,4'S)-2-(1-(4-nitrobenzyloxycarbonyl)-2-(2-allyloxycarbonyl-5-thienylcarbamoyl)pyrrolidin-4-ylthio)-6-(1-(tert-butyldimethylsilyloxy)ethyl)pen-2-em-3-carboxylate (450 mg, 0.52 mmol) in DMF (15 ml) was added triphenylphosphine (28 mg) and a solution of sodium 2-ethylhexanoate in ethyl acetate (2.6 ml, 1.2 mmol). Tetrakistriphenylphosphine (28 mg) was then added and the mixture stirred for 30 minutes. The mixture was evaporated to dryness and dissolved in ethyl acetate (25 ml) and water (25 ml) and hydrogenated in the presence of 10% palladium on carbon for two hours. The mixture was filtered through celite and the aqueous phase extracted with ethyl acetate then lyophilised. The residue was purified on a silica gel C18 column, eluting with 2–4% CH$_3$CN in (NH$_4$)$_2$SO$_4$ buffer (2 g/l). The fractions containing the product were evaporated and lyophilised to give the title product as a white solid (85 mg).

NMR (DMSO-d$_6$ +AcOD; 80° C.): δ1.16 (d, 3H); 1.75–1.85 (m, 1H), 2.55–2.65 (m, 1H); 2.75–2.85 (m, 1H); 3.4–3.5 (m, 1H); 3.6–3.7 (br, 1H); 3.7 (dd, 1H); 3.9–4.0 (m, 2H); 5.65 (d, 1H); 6.88 (d, 1H); 7.47 (d, 1H).

MS (FAB DMSO) M+H$^+$=486.

5-Nitro-2-thiophenecarboxylic acid.

The title compound was obtained from 2-thiophenecarboxylic acid, simultaneously with 4-nitro-2-thiophenecarboxylic acid, using the method described previously in example 1.

NMR (CDCl$_3$): δ7.65 (d, 1H); 7.88 (d, 1H).

Allyl 5-Nitro-2-thiophenecarboxylate

To a solution of 5-nitro-2-thiophenecarboxylic acid (20 g, 0.11 mol) in DMF (140 ml) were added sequentially allyl bromide (40 ml, 0.46 mol) and triethylamine (64 ml, 0.46 mol) with cooling to maintain the temperature of the reaction mixture below 30° C. After addition of the reagents, the reaction mixture was stirred for 3 hours at ambient temperature and then diluted with ethyl acetate. The solid which precipitated was filtered off, the filtrate washed with water, washed with saturated aqueous solution of sodium chloride, dried over MgSO$_4$and concentrated. The residue was purified by chromatography on silica gel using a mixture of CH$_2$C$_2$ - petroleum ether (3:7) as eluent to give the title compound as a white solid (8.8 g, 38%).

NMR (CDCl$_3$): δ4.84 (d, 2H); 5.36–5.45 (m, 2H); 6.00 (m, 1H); 7.71 (d, 1H); 7.88 (d, 1H).

Ally 5-amino-2-thiophenecarboxylate

To a solution of allyl 5-nitro-2-thiophenecarboxylate (3.2 g, 15 mmol) in concentrated hydrogen chloride (35 ml) was added, under cooling, SnCl$_2$.H$_2$O (10.1 g, 45 mmol). The mixture was stirred for 3.5 hours at ambient temperature, diluted with ethyl acetate and basified to pH 10 with 5N NaOH. The organic layer was washed with water and a saturated aqueous solution of sodium chloride, dried over HgSO$_4$ and concentrated. The residue was purified by chromatography on silica gel using a mixture of ethyl acetate and petroleum ether (3:7) to give the title compound as a yellow oil (1.94 g, 72%).

NHR (CDCl$_3$): δ4.34 (br s, 2H); 4.73 (d, 2H); 5.23 (d, 1H); 5.36 (d, 1H); 5.99 (m, 1H); 6.09 (d, 1H); 7.48 (d, 1H).

2S4S)-1-(4-Nitrobenzyloxycarbonyl)-2-(2-allyloxycarbonyl-5thienylcarbamoyl)pyrrolidine- 4-yltioacetate.

To a solution of (2S,4S)-4-acetylthio-2-carboxy-1-(4-nitrobenzyloxycarbonyl)pyrrolidine (3.79 g, 10.3 mmol) in CH$_2$Cl$_2$ (12 ml) were added thionyl chloride (3.75 ml, 51.5 mmol) anDHF (0.055 ml). The mixture was stirred for 16 hours at ambient temperature, concentrated and the residual oil taken up in CH$_2$Cl$_2$-toluene and reevaporated. The residue was dried under vacuum and solubilised in CH$_2$Cl$_2$ (25 ml). To this solution cooled to 0° C. was added N-diisopropylethylamine (2.05 ml, 11.8 mmol) and a solution of allyl 5-amino-2-thiophenecarboxylate (1.9 g, 10.3 mmol). After 15 minutes at ambient temperature, the solvent was evaporated and the residue taken up in a mixture of water and ethyl acetate. The organic layer was dried over HgSO$_4$ and evaporated to dryness. The residue was purified by chromatography on silica gel using a mixture of CH$_2$Cl$_2$-ether (9:1) to give the title compound as a yellow foam (4.68 g, 85%).

NMR (DMSO-d$_6$ +AcOD-d$_4$): δ2.33 (s, 3H); 2.80 (m, 1H); 3.38 (m, 1H); 4.00–4.15 (m, 2H); 4.52 (m, 2H); 4.77 (d, 2H); 5.02–5.42 (m, 4H); 6.00 (m, 1H); 6.77 (m, 1H); 7.45 (m, 1H); 7.60–7.68 (m, 2H); 7.95 (m, 1H); 8.23 (m, 1H).

(2S4S)-1-(4-Nitrobenzyloxycarbonyl)-2-(2-allyloxycarbony5-thienyl-carbamoyl)pyrrolidin-4-ylthio.

To a solution of (2S,4S)-1-(4-nitrobenzyloxycarbonyl)-2-(2-allyloxycarbonyl-5-thienylcarbamoyl)pyrrolidin-4-ylthioacetate (1.06 g, 2 mmol) in dichloromethane (2 ml) was added at 0° C. ethanol (0.8 ml, 4 mmol). The reaction mixture was stirred at ambient temperature for 1.5 hours and acidified to pH4 with 6N HCl. Ethyl acetate was added to the solution, the organic layer was washed with water and aqueous solution of sodium chloride, dried over MgSO$_4$ and evaporated to give the title compound as a yellow foam (0.96 g, 97%).

NMR (DMSO-d$_6$-TFA): δ1.87 (m, 1H); 2.73 (m, 1H); 3.29 (m, 1H); 3.44 (m, 1H), 4.01 (m, 1H); 4.42 (m, 1H); 4.72 (br s, 2H), 5.02–5.40 (m, 4H); 6.01 (m, 1H); 7.76 (m, 1H); 7.43 (d, 1H); 7.61–7.68 (m, 2H); 7.93 (d, 1H); 8.25 (d, 1H).

To a solution of (2S,4S)-1-(4-nitrobenzyloxycarbonyl)-2-(2-allyloxycarbonyl-5-thienylcarbamoyl)pyrrolidin-4-ylthiol (2.31 g, 4.49 mmol) in acetonitrile (15 ml) was added allyl (5R,6S,8R)-2-(ethylsulphonyl)-6-(1-(tert-butyldimethylsilyloxy)ethyl)pen-2-em-3carboxylate (1.74 g, 3.82 mmol), N-ethyldiisopropylamine (800 μl 4.58 mmol), tri-nt-butylphosphine (190 μl 0.76 mmol), water (14 μl 0.76 mmol). The mixture was stirred for one hour and the solvent evaporated. The residue was purified by flash chromatography eluting with 45–55% ethyl acetate in petroleum ether to give allyl (5R,6S,8R,2'S,4'S)-2-(1-(4-nitrobenzyloxycarbonyl)-2-(2-allyloxycarbonyl-5-thienylcarbamoyl)pyrrolidin-4-ylthio)-6-(1-(tert-butyldimethylsilyloxy)ethyl)pen-2-em-3-carboxylate as a pale yellow solid (1.1 g, 34%).

NMR (DMSO-d$_6$, 70° C.): δ0.0 (2S, 6H); 0.85 (s, 9H); 1.20 (d, 3H); 1.90–2.10 (br, 1H); 2.85–2.95 (br, 1H); 3.50–3.60 (br, 1H); 3.95–4.10 (br, 2H); 4.20–4.30 (m, 2H); 4.50–4.70 (m, 3H); 4.75 (m, 2H); 5.20–5.40 (m, 6H); 5.75 (s, 1H); 5.80–6.10 (m, 2H); 6.80 (d, 1H); 7.60 (d, 1H); 7.50–8.00 (br, 4H).

To a solution of allyl (5R,6S,8R,2'S,4'S)-2-(1-(4-Nitrobenzyloxycarbonyl)-2-(2-allyloxycarbonyl-5-thienylcarbamoyl)pyrrolidin-4-ylthio)-6-(1-(tert-butyldimethylsilyloxy)ethyl)pen-2-em-3carboxylate (1.1 g, 1.28 mmol) in THF (16 ml) at 0° C. were added acetic acid (1.46 ml, 25.6 mmol) then tetrabutylammonium fluoride in THF (12.8 ml, 1M, 12.8 mmol) portionwise. The mixture was left overnight at ambient temperature and concentrated to half volume by evaporating the solvent. The residue was diluted in ethyl acetate, washed twice with a saturated aqueous solution of sodium bicarbonate, once with water then brine, dried with MgSO$_4$ and the solvent evaporated. The residue was triturated with ether, filtered and dried under vacuum to give allyl (5R,6S,8R,2'S,4'S)-2-(1-(4-nitrobenzyloxycarbonyl)-2-(2-allyloxycarbonyl-5-thienylcarbamoyl)pyrrolidin-4-ylthio)-6-(1-hydroxyethyl)pen-2-em-3-carboxylate (800 mg).

NMR: δ(DMSO, 80° C.): δ1.2 (d, 3H); 2.00–2.10 (br, H); 2.85–2.95 (br, 1H); 3.50–3.60 (br, 1H); 3.80 (d, 1H); 3.95–4.05 (br, 2H); 4.15–4.25 (br, 1H); 4.50–4.75 (m, 5H); 5.15–5.40 (br, 6H); 5.75 (d, 1H); 5.80–6.05 (m, 2H); 6.75 (d, 1H); 7.60 (d, 1H); 7.50 and 8.00 (2 x br, 4H).

We claim:

1. A compound of the formula (I):

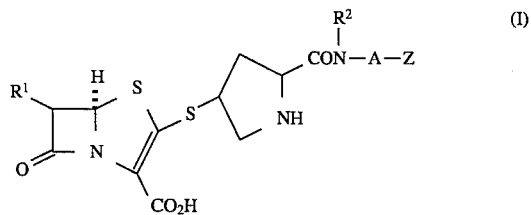

wherein:

R$^1$ is 1-hydroxyethyl, 1-fluoroethyl or hydroxymethyl;

R$^2$ is hydrogen or C$_{1-4}$alkyl;

Z is carboxy, sulfonic acid, tetrazol-5-yl or C$_{1-4}$alkylsulfonylcarbamoyl (—CONHSO$_2$C$_{1-4}$alkyl);

A is a phenyl or thienyl ring;

and A is optionally further substituted by one or two substituents selected from halo, cyano, C$_{1-4}$alkyl, nitro, hydroxy, carboxy, C$_{1-4}$alkoxy, trifluoromethyl, C$_{1-4}$alkoxycarbonyl, amino, C$_{1-4}$alkylamino, di-C$_{1-4}$alkylamino, sulfonic acid, C$_{1-4}$alkylS(O)$_n$—(wherein n is 0–2), C$_{1-4}$alkanoylamino, C$_{1-4}$alkanoyl(N-C$_{1-4}$alkyl)amino, carbamoyl, C$_{1-4}$alkylcarbamoyl, di-C$_{1-4}$alkylcarbamoyl, N-C$_{1-4}$alkanesulfonamido and tetramethylene;

or a pharmaceutically acceptable salt or in vivo hydrolysable ester thereof.

2. A compound according to claim 1 wherein R$^1$ is 1-hydroxyethyl.

3. A compound according to either claim 1 or claim 2 of the formula (IV):

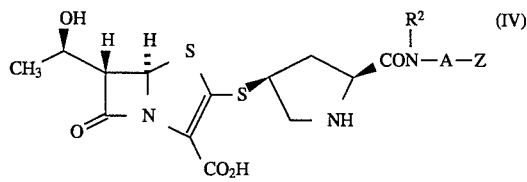

wherein R$^2$, Z, A and optional substituents on A are as defined in claim 1.

4. A compound according to claim 3 wherein Z is carboxy.

5. A compound according to claim 3 wherein optional substituents on A are selected from halo, cyano, C$_{1-4}$alkyl, nitro, hydroxy, carboxy, C$_{1-4}$alkoxy, carbamoyl, amino and trifluoromethyl.

6. A compound according to claim 1 which is (5R,6S,8R,2'S,4'S)-2-(2-(2-carboxy-4-thienylcarbamoyl)pyrrolidin-4-ylthio)-6-(1-hydroxyethyl)pen-2-em-3-carboxylic acid;

(5R,6S,8R,2'S,4'S)-2-(2-(3-carboxyphenylcarbamoyl)pyrrolidin-4-ylthio)-6 -(1-hydroxyethyl)pen-2-em-3-carboxylic acid;

(5R,6S,8R,2'S,4'S)-2-(2-(2-carboxy-5-thienylcarbamoyl)pyrrolidin-4-ylthio)-6-(1-hydroxyethyl)pen-2-em-3-carboxylic acid;

and pharmaceutically acceptable salts thereof.

7. A pharmaceutical composition which comprises a compound according to any one of claim 1 and a pharmaceutically acceptable carrier.

8. A method of treatment of an infection by administering an antibacterially effective amount of a compound of the formula (I) to a patient in need thereof.

* * * * *